United States Patent [19]

Ue et al.

[11] Patent Number: 5,301,087

[45] Date of Patent: Apr. 5, 1994

[54] ELECTROLYTE FOR ELECTROLYTIC CAPACITOR AND ELECTROLYTIC CAPACITOR USING THE SAME

[75] Inventors: Makoto Ue; Masayuki Takeda; Tomohiro Satoh, all of Ami, Japan

[73] Assignee: Mitsubishi Petrochemical Co., Ltd., Tokyo, Japan

[21] Appl. No.: 842,472

[22] Filed: Feb. 27, 1992

[30] Foreign Application Priority Data

Feb. 28, 1991 [JP] Japan ................................. 3-55618
Feb. 28, 1991 [JP] Japan ................................. 3-55742

[51] Int. Cl.$^5$ ................................. H01G 9/02
[52] U.S. Cl. ................................. 361/505; 361/506; 252/62.2; 429/194; 429/198
[58] Field of Search .............. 252/62.2; 429/198, 194; 562/500, 590; 361/505, 506, 508, 512, 516

[56] References Cited

U.S. PATENT DOCUMENTS

| | | | |
|---|---|---|---|
| 3,812,039 | 5/1974 | Niwa | 252/62.2 |
| 4,376,713 | 3/1983 | Dunkl | 252/62.2 |
| 4,522,737 | 6/1985 | MacNamee | 252/62.2 |

FOREIGN PATENT DOCUMENTS

| | | |
|---|---|---|
| 1-103821 | 4/1989 | Japan . |
| 2-54917 | 2/1990 | Japan . |
| 2-163920 | 6/1990 | Japan . |
| 2-298008 | 12/1990 | Japan . |

Primary Examiner—Prince Willis, Jr.
Assistant Examiner—Alan D. Diamond
Attorney, Agent, or Firm—Oblon, Spivak, McClelland, Maier & Neustadt

[57] ABSTRACT

Disclosed is an electrolyte for an electrolytic capacitor which comprises a salt of a tertiary dicarboxylic acid represented by the following formula (I) or (II):

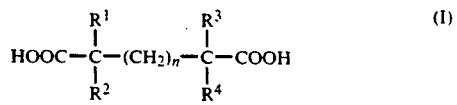

wherein n represents an integer of 1 to 5, and $R^1$ to $R^4$ each represents an alkyl group having 4 or less carbon atoms,

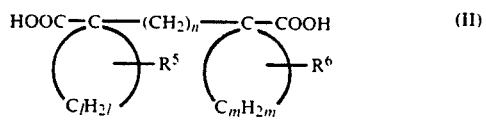

wherein n has the same meaning as defined above, l and m each represents an integer of 4 or 5, and $R^5$ and $R^6$ each represents hydrogen atom, methyl group or ethyl group, and an electrolytic capacitor using the same.

8 Claims, No Drawings

ELECTROLYTE FOR ELECTROLYTIC CAPACITOR AND ELECTROLYTIC CAPACITOR USING THE SAME

BACKGROUND OF THE INVENTION

This invention relates to an electrolyte for an electrolytic capacitor and an electrolytic capacitor using the same.

An electrolytic capacitor uses a so-called valve metal anode such as as aluminum and tantalum, on which an insulating oxide film is formed by anodic oxidation as a dielectric material. The electrolytic capacitor can be formed by placing a cathode opposed to the anode, interposing a separator between two electrodes and making retained an electrolyte to the separator.

Since the anode is subjected to etching treatment to enhance the surface area, the electrolyte functions as a true cathode by contacting with the concave and convex surface. Electric conductivity and temperature characteristics of the electrolyte become main factors to determine the electric characteristics of an electrolytic capacitor. Also, the electrolyte repairs damage of an oxide film whereby it affects to leakage current and lifetime of the capacitor. Thus, the electrolyte is the most important constitutional element which controls the characteristics of the electrolytic capacitor.

In the prior art, as an electrolyte for an electrolytic capacitor, particularly for a medium or high voltage, so-called ethylene glycol-boric acid type electrolyte has been used. This kind of the electrolyte forms water when heating by esterification reaction of ethylene glycol and boric acid. Therefore, there is a disadvantage that it cannot be used at a high temperature exceeding 100° C. since inner pressure is too heightened.

In order to overcome such a disadvantage, azelaic acid, sebacic acid, decanedicarboxylic acid or a salt of these acids has been used, but these materials are poor in solubility to a solvent such as ethylene glycol and also insufficient in thermal stability.

In Japanese Laid-Open Patent Application No. 116815/1986, there has been proposed the method for improving solubility and thermal stability by using a tertiary monocarboxylic acid, but anodic film forming ability is insufficient. In Japanese Laid-Open Patent Application No. 103821/1989, it has been proposed to use a tertiary dicarboxylic acid, but the compound contains ester bonds, which are subjected to scission, and results in the deterioration of the electrolyte.

SUMMARY OF THE INVENTION

An object of the present invention is to improve thermal stability of a conventional electrolyte and solubility of a solute and to provide an electrolytic capacitor having excellent properties.

The present inventors have studied about a solute to be used in an electrolyte and found a salt of a tertiary dicarboxylic acid as a compound which satisfies the following conditions:

(1) solubility is improved by incorporating a branched carbon chain structure (particularly unsymmetrical structure) whereby improving electric conductivity.

(2) film forming ability is improved by incorporating two carboxyl groups, (3) a substituent is introduced at the position next to the carboxyl group in order to inhibit esterification with ethylene glycol sterically, and (4) skeleton is formed only by methylene chain except for the two carboxyl groups without introducing any functional group which causes deterioration,
whereby accomplished the present invention.

The present invention is an electrolyte for an electrolytic capacitor which comprises a salt of a tertiary dicarboxylic acid represented by the following formula (I) or (II):

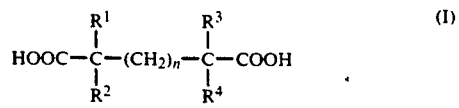

wherein n represents an integer of 1 to 5, and $R^1$ to $R^4$ each represents an alkyl group having 4 or less carbon atoms,

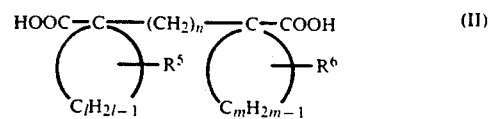

wherein n has the same meaning as defined above, l and m each represents an integer of 4 or 5, and $R^5$ and $R^6$ each represents hydrogen atom, methyl group or ethyl group, and an electrolytic capacitor comprising a capacitor element and the above electrolyte impregnated to the element.

DESCRIPTION OF THE PREFERRED EMBODIMENTS

In the following, the present invention is described in more detail.

In the above formula (I), as the alkyl group having 4 or less of carbon atoms represented by $R^1$ to $R^4$, there may be mentioned methyl group, ethyl group, propyl group, isopropyl group, butyl group and isobutyl group, and $R^1$ to $R^4$ may be the same or different from each other.

Specific examples of the tertiary dicarboxylic acid represented by the formula (I) may include, for example, 2,2,4,4-tetramethylglutaric acid, 2,2,5,5-tetramethyladipic acid, 2,2,6,6-tetramethylpimelic acid, 2,2,7,7-tetramethylsuberic acid, 2,2,8,8-tetramethylazelaic acid, 2,2,4,4-tetraethylglutaric acid, 2,2,5,5-tetraethyladipic acid, 2,2,6,6-tetraethylpimelic acid, 2,2,7,7-tetraethylsuberic acid, 2,2,8,8-tetraethylazelaic acid, 2,2,4,4-tetrapropylglutaric acid, 2,2,5,5-tetrapropyladipic acid, 2,2,6,6-tetrapropylpimelic acid, 2,2,3,3-tetrapropylsuberic acid, 2,2,8,8-tetrapropylazelaic acid, 2,2,4,4-tetrabutyl-glutaric acid, 2,2,5,5-tetrabutyladipic acid, 2,2,6,6-tetrabutylpimelic acid, 2,2,7,7-tetrabutylsuberic acid, 2,2,8,8-tetrabutylazelaic acid, 2,2,4-trimethyl-4-ethyl-glutaric acid, 2,2,5-trimethyl-5-ethyladipic acid, 2,2,6-trimethyl-6-ethylpimelic acid, 2,2,7-trimethyl-7-ethyl -suberic acid, 2,2,8-trimethyl-8-ethylazelaic acid, 2,2-dimethyl-4,4-diethylglutaric acid, 2,2-dimethyl-5,5-diethyladipic acid, 2,2-dimethyl-6,6-diethylpimelic acid, 2,2-dimethyl-7,7-diethylsuberic acid, 2,2-dimethyl-8,8 -diethylazelaic acid. 2,4-dimethyl-2,4-diethylglutaric acid, 2,5-dimethyl-2,5-diethyladipic acid, 2,6-dimethyl-2,6-diethylpimelic acid, 2,7-dimethyl-2,7-diethylsuberic acid, 2,8-dimethyl-2,8-diethylazelaic acid, 2-methyl-2,4,4-triethylglutaric acid, 2-methyl-2,5,5-triethyladipic acid, 2-methyl-2,6,6-triethylpimelic acid, 2-methyl-2,7,7-triethylsuberic acid, 2-methyl-2,8,8-triethylazelaic acid, 2,2,4-trimethyl-4-propylglutaric acid, 2,2,5-trimethyl-5-propyladipic acid, 2,2,6-trimethyl-6-propylpimelic acid, 2,2,7-trimethyl-7-propylsuberic acid, 2,2,8-trimethyl-8-propylazelaic acid, 2,2-dimethyl-4,4-dipropylglutaric acid, 2,2-dimethyl-5,5-dipropyladipic acid, 2,2-dimethyl-6,6-dipropylpimelic acid, 2,2-dimethyl-7,7-dipropylsuberic acid, 2,2-dimethyl-8,8-dipropylazelaic acid, 2,4-dimethyl-2,4-dipropylglutaric acid, 2,5-dimethyl-2,5-dipropyladipic acid, 2,6-dimethyl-2,6-dipropylpimelic acid, 2,7-dimethyl-2,7-dipropylsuberic acid, 2,8-dimethyl-2,8-dipropylazelaic acid, 2-methyl-2,4,4-tripropylglutaric acid, 2-methyl-2,5,5-tripropyladipic acid, 2-methyl-2,6,6-tripropylpimelic acid, 2-methyl-2,7,7-tripropylsuberic acid, 2-methyl-2,8,8-tripropylazelaic acid, 2,2,4-trimethyl-4-butylglutaric acid, 2,2,5--trimethyl-5-butyladipic acid, 2,2,6-trimethyl 6-butylpimelic acid, 2,2,7-trimethyl-7-butylsuberic acid, 2,2,8-trimethyl-8-butylazelaic acid, 2,2-dimethyl-4,4-dibutylglutaric acid, 2,2-dimethyl-5,5-dibutyladipic acid, 2,2-dimethyl-6,6-dibutylpimelic acid, 2,2-dimethyl-7,7-dibutylsuberic acid, 2,2-dimethyl-8,8-dibutylazelaic acid, 2,4-dimethyl-2,4-dibutylglutaric acid, 2,5-dimethyl-2,5-dibutyladipic acid, 2,6-dimethyl-2,6-dibutylpimelic acid, 2,7-dimethyl-2,7-dibutylsuberic acid, 2,8-dimethyl-2,8-dibutylazelaic acid, 2-methyl-2,4,4-tributylglutaric acid, 2-methyl-2,5,5-tributyladipic acid, 2-methyl-2,6,6-tributylpimelic acid, 2-methyl-2,7,7-tributylsuberic acid, 2-methyl-2,8,8-tributylazelaic acid, 2,2,4-triethyl-4-propyl-glutaric acid, 2,2,5-triethyl-5-propyladipic acid, 2,2,6-triethyl-6-propylpimelic acid, 2,2,3-triethyl-7-propyl-suberic acid, 2,2,8-triethyl-8-propylazelaic acid, 2,2-diethyl-4,4-dipropylglutaric acid, 2,2-diethyl-5,5-dipropyladipic acid, 2,2-diethyl-6,6-dipropylpimelic acid, 2,2-diethyl-7,7-dipropylsuberic acid, 2,2-diethyl-8,8-dipropylazelaic acid, 2,4-diethyl-2,4-dipropylglutaric acid, 2,5-diethyl-2,5-dipropyladipic acid, 2,6-diethyl-2,6-dipropylpimelic acid, 2,7-diethyl-2,7-dipropylsuberic acid, 2,8-diethyl-2,8-iipropylazelaic acid, 2-ethyl-2,4,4-tripropyl-glutaric acid, 2-ethyl-2,5,5-tripropyladipic acid, 2-ethyl-2,6,6-tripropylpimelic acid, 2-ethyl-2,3,7-tripropylsuberic acid, 2-ethyl-2,8,8-tripropylazelaic acid, 2,2,2-triethyl-4-butylglutaric acid, 2,2,2-triethyl-5-butyladipic acid, 2,2,2-triethyl-6--butylpimelic acid, 2,2,2-triethyl-7-butyl-suberic acid, 2,2,2-triethyl-8-butylazelaic acid, 2,2-diethyl-4,4-dibutylglutaric acid, 2,2-diethyl-5,5-dibutyladipic acid, 2,2-diethyl-6,6-dibutylpimelic acid, 2,2-diethyl-7,7-dibutylsuberic acid, 2,2-diethyl-8,8-dibutylazelaic acid, 2,4-diethyl-2,4-dibutylglutaric acid, 2,5-diethyl-2,5-dibutyladipic acid, 2,6-diethyl-2,6-dibutylpimelic acid, 2,7-diethyl-2,7-dibutylsuberic acid, 2,8-diethyl-2,8-dibutylazelaic acid, 2-ethyl-2,4,4-tributylglutaric acid, 2-ethyl-2,5,5-tributyladipic acid, 2-ethyl-2,6,6-tributylpimelic acid, 2-ethyl-2,7,7-tributylsuberic acid, 2-ethyl-2,8,8-tributylazelaic acid, 2,2,4-tripropyl-4-butylglutaric acid, 2,2,5-tripropyl-5-butyladipic acid, 2,2,6-tripropyl-6-butylpimelic acid, 2,2,7-tripropyl-7-butylsuberic acid, 2,2,8-tripropyl-8-butylazelaic acid, 2,2-dipropyl-4,4-dibutylglutaric acid, 2,2-dipropyl-5,5-dibutyladipic acid, 2,2-dipropyl-6,6-dibutylpimelic acid, 2,2-dipropyl-7,7-dibutylsuberic acid, 2,2-dipropyl-8,8-dibutylazelaic acid, 2,4-dipropyl-2,4-dibutylglutaric acid, 2,5-dipropyl-2,5-dibutyladipic acid, 2,6-dipropyl-2,6-dibutylpimelic acid, 2,3-dipropyl-2,7-dibutylsuberic acid, 2,8-dipropyl-2,8-dibutylazelaic acid, 2-propyl-2,4,4-tri-butylglutaric acid, 2-propyl-2,5,5-tributyladipic acid, 2-propyl-2,6,6-tributylpimelic acid, 2-propyl-2,7,7-tributyl -suberic acid, 2-propyl-2,8,8-tributylazelaic acid, 2,2-dimethyl-4-ethyl-4-propylglutaric acid, 2,5-dimethyl-2-ethyl-5-propyladipic acid, 2-methyl-2-ethyl-4-propyl-4-butylglutaric acid, 2-methyl-2-butyl-5-ethyl-5-propyladipic acid and 2-methyl-2-propyl-6-ethyl-6-butylpimelic acid.

As the specific examples of the tertiary dicarboxylic acid represented by the formula (II) may include, for example, 2,2-tetramethylene-4,4-tetramethyleneglutaric acid, 2,2-tetramethylene-5,5-tetramethyleneadipic acid, 2,2-tetra -methylene-6,6-tetramethylenepimelic acid, 2,2-tetramethylene-7,7-tetramethylenesuberic acid, 2,2-tetramethylene-8,8-tetramethyleneazelaic acid, 2,2-tetramethylene-4,4-pentamethyleneglutaric acid, 2,2-tetramethylene-5,5-pentamethyleneadipic acid, 2,2-tetramethylene-6,6-pentamethylenepimelic acid, 2,2-tetramethylene-7,7-pentamethylenesuberic acid, 2,2-tetramethylene-8,8-pentamethyleneazelaic acid, 2,2-pentamethylene-4,4-pentamethylenealutaric acid, 2,2-pentamethylene-5,5-pentamethyleneadipic acid, 2.2-pentamethylene-6,6-pentamethylenepimelic acid, 2,2-pentamethylene-7,7-pentamethylenesuberic acid, 2,2-pentamethylene-8,8-pentamethyleneazelaic acid,

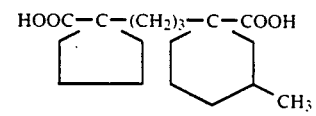

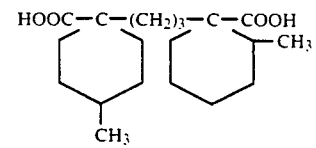

and

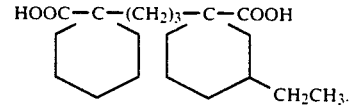

These carboxylic acid may be used singly or in combination as a mixture. In the above formula (I), those in which the alkyl groups for $R^1$ to $R^4$ are different from each other, or in the above formula (II), those having a cyclopentane ring or cyclohexane ring to which an alkyl group is substituted at 2-position or 3-position become a mixture of optical isomers, but generally unsymmetrical one has better solubility to a solvent. Also, when the carbon number increases, solubility generally tends to become poor.

As a salt of the tertiary dicarboxylic acid to be used in the present invention, there may be mentioned, for example, an ammonium salt, an amine salt, a quaternary ammonium salt, a phosphonium salt or a sulfonium salt of the above carboxylic acids.

As a solvent which dissolves the salt of the tertiary dicarboxylic acid to be used in the present invention, there may be mentioned, for example, amide solvents such as N-methylformamide, N-ethylformamide, N,N-dimethylformamide, N,N-diethylformamide, N-ethylacetamide, N,N -dimethylacetamide and N-methylpyrrolidinone; lactone solvents such as γ- butyrolactone, γ-valerolactone and δ-valerolactone; carbonate solvents such as ethylene carbonate, propylene carbonate and butylene carbonate; alcohol solvents such as ethylene glycol, glycerin and methyl cellosolve; nitrile solvents such as 3-methoxypropionitrile and glutaronitrile; and phosphate solvents such as trimethylphoschate and triethylphosphate; and a mixture of the above solvents.

A dissolved amount of the salt of the tertiary dicarboxylic acid to the above solvent may vary depending on the electric conductivity of an electrolyte to be obtained, but it is generally less than saturation concentration, preferably 1 to 25 % by weight.

In the electrolyte of the present invention, in addition to the above salt of the tertiary dicarboxylic acid and the solvent, various additives such as phosphoric acid derivative and nitrobenzene derivatives may be added in order to prevent electrolytic corrosion, decrease leakage current and absorb hydrogen gas.

Also, in the range which does not inhibit the problem of the present invention, if necessary, 1 to 10 % by weight of water may be added in order to improve electric conductivity and improve film forming ability.

The salt of the tertiary dicarboxylic acid to be used as the solute in the present invention has good solubility to a solvent, and the electrolyte containing the salt can maintain relatively high electric conductivity and spark voltage, and has high thermal stability so that a middle/high voltage electrolytic capacitor having long lifetime can be obtained.

EXAMPLES

In the following, the present invention will be described by referring to Examples and Comparative examples, but the present invention is not limited by these examples.

EXAMPLE 1

In ethylene glycol was dissolved 10 % by weight of diammonium 2,2,6,6-tetramethylpimelate to prepare an electrolyte.

The electric conductivity of the electrolyte was 1.8 mS/cm at 25° C. and the spark voltage when 5 mA/cm$^2$ of a constant current was applied to an aluminum electrode was 430 V.

EXAMPLE 2

In the same manner as in Example 1, an electrolyte was prepared except for replacing the solute with diammonium 2,2,8,8-tetramethylazelate, and the electric conductivity and spark voltage were measured. The electric conductivity was 1.7 mS/cm and the spark voltage was 440 V.

EXAMPLE 3

In the same manner as in Example 1, an electrolyte was prepared except for replacing the solute with diammonium 2,6-diethyl-2,6-dibutylpimelate, and the electric conductivity and spark voltage were measured. The electric conductivity was 1.3 mS/cm and the spark voltage was 485 V.

EXAMPLE 4

In the same manner as in Example 1, an electrolyte was prepared except for replacing the solute with diammonium 2,6-dimethyl-2,6-dibutylpimelate, and the electric conductivity and spark voltage were measured. The electric conductivity was 1.2 mS/cm and the spark voltage was 470 V.

Next, the electrolyte was sealed in a tube and allowed to stand at 110° C. for 1000 hours, and then the electric conductivity of the electrolyte was measured. The electric conductivity was 1.2 mS/cm and no deterioration was admitted.

EXAMPLE 5

In the same manner as in Example 1, an electrolyte was prepared except for replacing the solute with diammonium 2,7-dimethyl-2,7-diethylsuberate, and the electric conductivity and spark voltage were measured. The electric conductivity was 1.2 mS/cm and the spark voltage was 490 V.

Next, the electrolyte was sealed in a tube and allowed to stand at 110° C. for 1000 hours, and then the electric conductivity of the electrolyte was measured. The electric conductivity was 1.2 mS/cm and no deterioration was admitted.

EXAMPLE 6

In ethylene glycol was dissolved 14 % by weight of diammonium 2,2,7,7-tetramethylsuberate to prepare an electrolyte. The electric conductivity of the electrolyte was 1.9 mS/cm and the spark voltage was 430 V.

EXAMPLE 7

In ethylene glycol solvent was dissolved 7 % by weight of diammonium 2,2-pentamethylene-6,6-pentamethylenepimelate to prepare an electrolyte. The electric conductivity of the electrolyte was 1.0 mS/cm and the spark voltage was 460 V.

Next, the electrolyte was sealed in a tube and allowed to stand at 110° C. for 1000 hours, and then the electric conductivity of the electrolyte was measured. The electric conductivity was 1.0 mS/cm and no deterioration was admitted.

COMPARATIVE EXAMPLE 1

In the same manner as in Example 1, an electrolyte was prepared except for replacing the solute with ammonium borate, and the electric conductivity and spark voltage were measured. The electric conductivity was 1.1 mS/cm and the spark voltage was 450 V.

Next, the electrolyte was sealed in a tube and allowed to stand at 110° C. for 1000 hours, and then the electric conductivity of the electrolyte was measured. The electric conductivity was 0.8 mS/cm and deterioration of the electrolyte was admitted.

COMPARATIVE EXAMPLE 2

In the same manner as in Example 1, an electrolyte was prepared except for replacing the solute with diammonium salt of the tertiary dicarboxylic acid represented by the following formula:

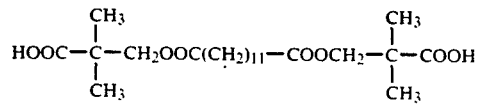

described in Japanese Laid-Open Patent Application No. 103821/1989, and the electric conductivity and spark voltage were measured. The electric conductivity was 1.0 mS/cm and the spark voltage was 495 V.

Next, the electrolyte was sealed in a tube and allowed to stand at 110° C. for 1000 hours, and when cooled to room temperature, it was solidified due to deterioration.

When this deteriorated material was analyzed by $^1$H-NMR analyzer, it was found that ester bonds in the solute molecules had been completely broken.

EXAMPLE 8

By using the electrolyte prepared in Example 4, an aluminum electrolytic capacitor having a diameter of 10 mm and a height of 20 mm with rated working voltage of 450 V and nominal capacitance of 2.2 μF was prepared. Capacitance, dielectric loss (tan δ) and leakage current (5 minutes value) of the capacitor were 2.34 μF, 0.055 and 41 μA, respectively.

We claim:

1. An electrolyte solution for an electrolyte capacitor which comprises a diammonium salt of a tertiary dicarboxylic acid represented by the following formula (I) or (II) below dissolved in ethylene glycol:

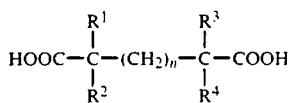

wherein n represents an integer of 2 to 5, and $R^1$ to $R^4$ each represents an alkyl group having 4 or less carbon atoms,

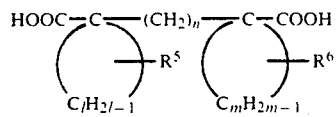

wherein n has the same meaning as defined above, l and m each represents an integer of 4 or 5, and $R^5$ and $R^6$ each represents hydrogen atom, methyl group or ethyl group.

2. The electrolyte according to claim 1, wherein $R^1$ to $R^4$ in the compound of the formula (I) each represents methyl group, ethyl group, propyl group, isopropyl group, butyl group or isobutyl group.

3. The electrolyte according to claim 1, wherein said salt is contained in said ethylene glycol an amount of 1 to 25% by weight.

4. An electrolytic capacitor comprising an anode, a cathode and a separator arranged between the anode and cathode, said separator impregnated with an electrolyte comprising ethylene glycol and a solute dissolved therein, said solute being a diammonium salt of a tertiary dicarboxylic acid represented by the following formula (I) or (II):

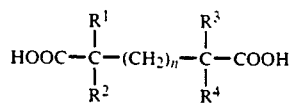

wherein n represents an integer of 2 to 5, and $R^1$ to $R^4$ each represents an alkyl group having 4 or less carbon atoms,

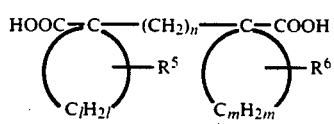

wherein n has the same meaning as defined above, and l and m each represents an integer of 4 or 5, and $R^5$ and $R^6$ each represents hydrogen atom, methyl group or ethyl group.

5. The electrolytic capacitor according to claim 4, wherein $R^1$ and $R^4$ in the compound of the formula (I) each represents methyl group, ethyl group, propyl group, isopropyl group, butyl group or isobutyl group.

6. The electrolytic capacitor according to claim 4, wherein said salt is contained in an amount of 1 to 25% by weight in said ethylene glycol.

7. An electrolyte solution for an electrolytic capacitor, consisting of diammonium salt of a tertiary dicarboxylic acid represented by formula (I) below dissolved in ethylene glycol:

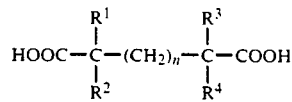

wherein n represents an integer of 2 to 5, and $R^1$ and $R^4$ each represents an alkyl group having four or less carbon atoms.

8. An electrolytic capacitor comprising an anode, a cathode and a separator arranged between the anode and cathode, said separator impregnated with an electrolyte, wherein said electrolyte consists of a diammonium salt of a tertiary dicarboxylic acid represented by formula I below dissolved in ethylene glycol:

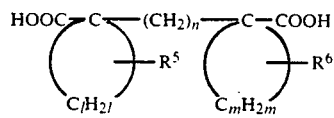

wherein n represent an integer of 2 to 5, and $R^1$ and $R^4$ each represents an alkyl group having four or less carbon atoms.

* * * * *